(12) United States Patent
Suzuki et al.

(10) Patent No.: US 11,672,220 B2
(45) Date of Patent: Jun. 13, 2023

(54) **SELF-COMPATIBLE *BRASSICA OLERACEA* PLANT AND METHOD FOR PRODUCING SAME**

(71) Applicant: SAKATA SEED CORPORATION, Yokohama (JP)

(72) Inventors: Takao Suzuki, Kanagawa (JP); Atsushi Izumida, Kanagawa (JP); Tetsuya Hiramoto, Kanagawa (JP)

(73) Assignee: SAKATA SEED CORPORATION

( * ) Notice: Subject to any disclaimer, the term of this patent is extended or adjusted under 35 U.S.C. 154(b) by 0 days.

(21) Appl. No.: 16/971,490

(22) PCT Filed: Feb. 22, 2019

(86) PCT No.: PCT/JP2019/006826
§ 371 (c)(1),
(2) Date: Oct. 30, 2020

(87) PCT Pub. No.: WO2019/163954
PCT Pub. Date: Aug. 29, 2019

(65) Prior Publication Data
US 2021/0051873 A1     Feb. 25, 2021

(30) Foreign Application Priority Data
Feb. 23, 2018  (JP) .............................. JP2018-030872

(51) Int. Cl.
*A01H 5/10*     (2018.01)
*A01H 6/20*     (2018.01)
*C12Q 1/6895*   (2018.01)

(52) U.S. Cl.
CPC ............... *A01H 6/203* (2018.05); *A01H 5/10* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

FOREIGN PATENT DOCUMENTS

WO        2014-115680 A1    7/2014

OTHER PUBLICATIONS

Nasrallah, Genetics 76: 45-50, 1975 (Year: 1975).*
Sequence Accession D85205, Jul. 24, 2016, sequence alignment provided at the end of the office action. (Year: 2016).*
Thierry Gaude, et al., "Expression of a Self-Incompatibility Gene in a Self- Compatible Line of *Brassica oleracea*", The Plant Cel l, 1993, vol. 5, pp. 75-86 (13 pages).
Lei Tian, et al., "Identification of S haplotypes in cabbage inbred lines (*Brassica oleracea* var. *capitata* L.)", Scientia Horticulturae, 2013, vol. 164, pp. 400-408 (9 pages).
Piotr Kaminski., "Development of male sterile broccoli lines with Raphanus sativus cytoplasm and assessment of their value for breeding purposes.", Journal of Horticultural Research, 2013, vol. 21 (2), pp. 101-107 (7 pages).
Makoto Kusaba, et al., "Striking sequence similarity in inter- and intra-specific comparisons of class I SLG alleles from *Brassica oleracea* and *Brassica campestris*: Implications for the evolution and recognition mechanism.", Proc. Natl. Acad. Sci. USA, Jul. 1997, vol. 94, pp. 7673-7678 (6 pages).
International Search Report issued for corresponding International Application No. PCT/JP2019/006826, dated May 14, 2019 (4 pages).
Database Genbank (Online); Kusaba M. et al. "Striking sequence similarity in inter- and intra-specific comparisons of class 1 SLG alleles from *Brassica oleracea* and *Brassica campestris*: Implications for the evolution and recognition mechanism"; XP055856112, Database Accession No. D85205; published on Jul. 8, 1997 (total 1 page).
Hiroyasu Kitashiba and June B. Nasrallah "Self-incompatibility in Brassicaceae crops: lessons for interspecific incompatibility"; Breeding Science; vol. 64, No. 1; Published on Jan. 1, 2014; pp. 23-37 (total 15 pages).
Supplementary European Search Report issued for the corresponding European Patent Application No. EP19756952.8; dated Nov. 9, 2021 (total 7 pages).
June B. Nasrallah, et al. "Genetic evidence for the requirement of the *Brassica* S-locus receptor kinase gene in the self-incompatiblity response"; The Plant Journal; Section of Plant Biology, Division of Biological Sciences, Cornell Iniversity, Ithaca, NY; Year 1994 (total 12 pages).

* cited by examiner

*Primary Examiner* — Elizabeth F McElwain
(74) *Attorney, Agent, or Firm* — Harness, Dickey & Pierce, P.L.C.

(57) ABSTRACT

A *Brassica oleracea* plant is provided having self-compatibility, or a progeny thereof, wherein the plant excludes cauliflower and Chinese kale. For example, a *Brassica oleracea* plant having self-compatibility is provided. Thereby, technical means that makes it possible to accomplish stable and efficient production of parental line seeds for a *Brassica oleracea* plant can be provided.

5 Claims, 7 Drawing Sheets

Specification includes a Sequence Listing.

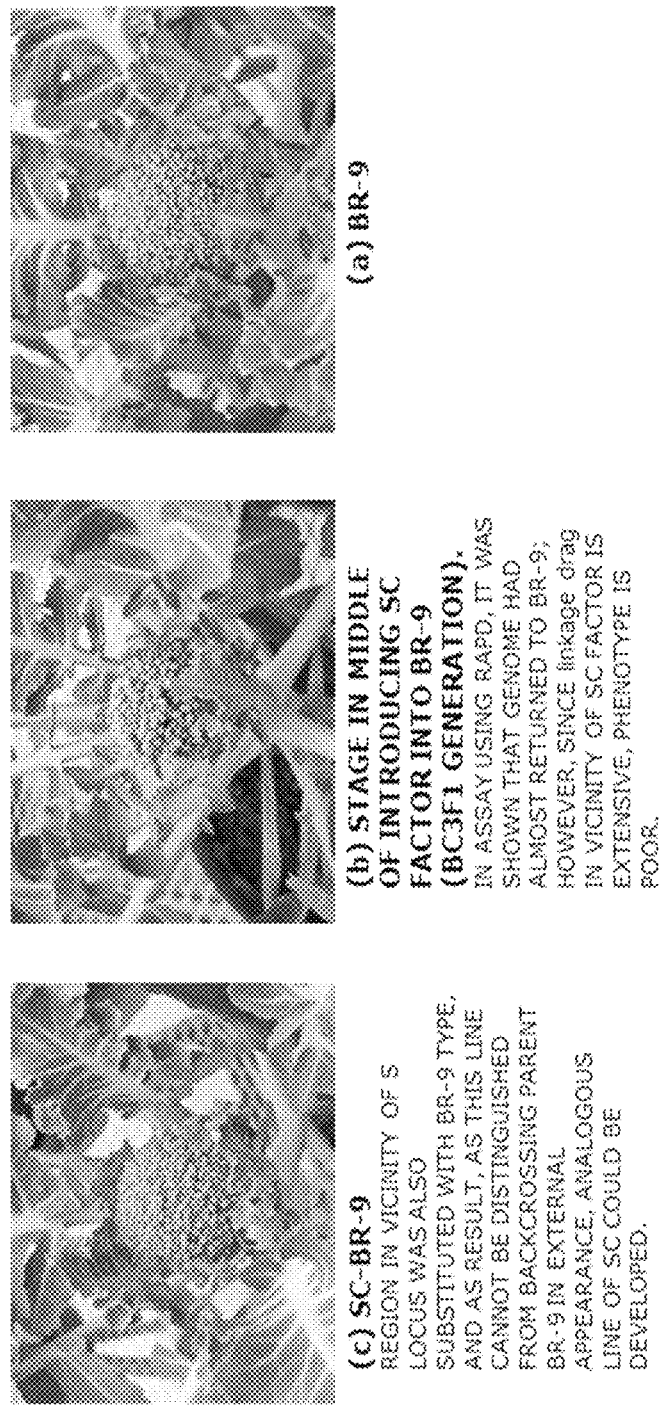

CMS-SC-BR-6     SC-BR-6
(A line)         (B line)

(A) REGARDING STAGE OF OPEN FLOWER
POLLINATION (OP) AND BUD POLLINATION (BP)

(B) STATE OF SEED SETING AT TIME POINT WHERE ONE MONTH HAS ELAPSED AFTER MATING

FIG. 5C

INVESTIGATION OF SEED ENTRY OF SI SYSTEM/SC SYSTEM

| MATING METHOD | CABBAGE PARENTAL LINE CB-3 (SI LINE) | | LINE OBTAINED BY INTRODUCING SC INTO CABBAGE PARENTAL LINE CB-3 | |
|---|---|---|---|---|
| | self pollination | | self pollination | |
| | BRANCH 1 | BRANCH 2 | BRANCH 1 | BRANCH 2 |
| BP10 | 9 | 12 | 6 | 6 |
| BP9 | 13 | 10 | 6 | 11 |
| BP8 | 10 | 9 | 14 | 13 |
| BP7 | 8 | 14 | 11 | 19 |
| BP6 | 4 | 10 | 9 | 13 |
| BP5 | 0 | 15 | 5 | 15 |
| BP4 | 0 | 6 | 8 | 16 |
| BP3 | 0 | 14 | 4 | 8 |
| BP2 | 0 | 10 | 15 | 16 |
| BP1 | 0 | 1 | 20 | 0 |
| OP1 | 0 | 0 | 18 | 17 |
| OP2 | 0 | 0 | 13 | 10 |
| OP3 | 0 | 0 | 16 | 14 |
| OP4 | 0 | 0 | 20 | 14 |
| OP5 | 0 | 0 | 12 | 16 |
| OP6 | 0 | 0 | 11 | 14 |
| OP7 | 0 | 0 | 18 | 19 |
| OP8 | 0 | 0 | 13 | 16 |
| OP9 | 0 | 0 | 15 | 20 |
| OP10 | 0 | 0 | 17 | 13 |
| OP11 | 0 | 0 | 13 | 15 |
| OP12 | 1 | 0 | 23 | 17 |
| OP13 | 0 | 0 | 19 | 15 |
| OP14 | 0 | 0 | 16 | 14 |
| OP15 | 1 | 0 | 21 | 14 |

(C) NUMBER OF SEEDS SET IN EACH POD

SEQUENCE LISTING

<160> NUMBER OF SEQ ID NOS: 15

<210> SEQ ID NO 1
<211> LENGTH: 1173
<212> TYPE: DNA
<213> ORGANISM: Brassica oleracea

<400> SEQUENCE: 1

```
tctttctcgt cttgattcta tttcgtcctg tcttttcgat caacattttg tcgtccacag      60
aatctcttac aatctcaggc aacggaacgc ttgtatctcc cggtgatgtc ttcgagctcg     120
gtttcttcag aaccacctca agttctcgtt ggtatctcgg gatatggtac aagaaagtct     180
acttcagaac ctacgtatgg gttgccaaca gagataaccc tctctcccgt tccattggaa     240
ccctcacaat ctccaacatg aacctggtcc tccttgatca ctctaataaa tctgtttggt     300
cgacaaatct tactagagaa aatgagagat ctccggtggt ggcagagctt ctcgctaacg     360
gaaatttcgt gatgcgagac tccaataaca acgacgcaag tggattctta tggcaaagtt     420
tcgatttccc tacagatacc ttgcttccag agatgaagct aggttacaac ctcaaaacag     480
ggctgaacag attccttaca gcatggagaa attcagatga tccctcaagc ggggattact     540
cgtacaagct tgaaaaccga gagcttcctg agttctatct actgaaaagt ggcttccaag     600
tccaccggag cggtccatgg aatggagtcc gatttagtgg cataccagag aaccaaaagt     660
tgagttacat ggtgtacaat ttcacagaga acagtgagga ggtcgcttat acatttcgaa     720
tgaccaacaa cagcttctac tcgagattga aagtaagttc cgacgggtac ttgcagcgac     780
tgacgttgat cccgatatca attgtttgga acttgttctg gtcttcacca gtggatatcc     840
ggtgtgatat gttcagggtt tgtggtcctt acgcttactg tgacgggaac acatcaccgt     900
tgtgtaactg tatccaaggg tttgatccct ggaatttgca gcagtgggat atcggggagc     960
cggcaggtgg gtgtgtaagg aggacgctgc tgagctgcag tggtgatggt tttaccaaga    1020
tgaagaaaat gaagttgcct gacactaggt tggcgattgt tgaccggagt attggtctga    1080
aagaatgtga gaagaggtgc cttagcgact gtaactgtac cgcatttgca aatgcggata    1140
tccggaatgg tggtacgggt tgtgtgattt gga                                 1173
```

<210> SEQ ID NO 2
<211> LENGTH: 1158
<212> TYPE: DNA
<213> ORGANISM: Brassica oleracea

<400> SEQUENCE: 2

```
tcttttttggt cttgattcca tttcgtcctg ccttttcgat caacattttg tcgtctacag      60
```

```
aatctcttac aatttcaaac aacagaacac ttgtatctcc cggtgatgtc ttcgagctcg      120
gtttcttcag aaccaattca agttctcctt ggtatctcgg gatatggtac aagcaattat      180
ccgacagaac ctatgtatgg gttgccaaca gagatagccc tctctccaac gccattggaa      240
tcctcaaaat ctctggcaat aatcttgtca tccttgatca ttccaataaa tctgtttggt      300
caacgaatat aactagagga aatgatagat ctccggtggt ggcagagctt ctcgctaatg      360
gaaacttcgt gatgcgacac gcaagtggat tcttgtggaa aagtttcgat taccctacag      420
atacattgct tccagagatg aagctgggtt acgacctcaa aacaaggttg aacaggttcc      480
ttatatcatg gagaagttta gatgatccgt caagcgggga ttacttgtac aagctcgaaa      540
accgaaggtt tcctgaattt tatctatcaa gtgggggctt tcaattgtat cggagtggtc      600
catggaatgg agtccgattt agtggcatac cagatgacca aaagttgagt tacatggtgt      660
acaatttcac agagaatagt gaagaagtcg cttatacatt ccgaatgacc aacaacagca      720
tgtactcgag attgacagta aatttcttag gggattttga acgacagacg tggaatccgt      780
cattagggat gtggaacagg ttttgggctt ttccattgga ctcacagtgc gatgcgtacg      840
gagcgtgtgg acctaacgct tactgtgacg tgaacacatc accgatttgt aactgtatcc      900
aagggttcaa tccctcgaat gtgcagcagt gggatcagag agtctggtca ggtgggtgta      960
taaggaggac gaggcttagc tgcagaggag atggttttac caggatgaaa aatatgaagt     1020
tgccagaaac tacgatggct actgtcgacc gcagtattgg tgtgaaagaa tgtgagaaga     1080
ggtgtcttag cgactgtaat tgtaccgcgt ttgcaaatgc ggatatccgg aatggtggga     1140
cgggttgtgt gatttgga                                                   1158
```

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
atgaaaggcg taagaaaaac cta                                               23

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
ccgtgtttta ttttaagaga aagagct                                           27

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
atcgatggga tgaaaaagtc atcg                                              24

<210> SEQ ID NO 6
<211> LENGTH: 24
<212> TYPE: DNA
<213> ORGANISM: Artificial Sequence

```
<220> FEATURE:
<223> OTHER INFORMATION: Primer

<400> SEQUENCE: 6
ctgctgatca tgttctgcct ctgg                                            24

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
caatcccaaa atccgagatc t                                               21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
atgaaagggg tacagaacat                                                 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctcaagtccc actgctgcgg                                                 20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
agccgttcag agacctttag a                                               21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cgttcaggag caaatgcaac                                                 20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gccaaagaga ggtgacaaat gg                                              22
```

```
<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
gcatcaatga atactcaaag agca                                          24

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
atcaggccac taggaaacct t                                             21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
actcatgttc cccgtgtagt t                                             21
```

SELF-COMPATIBLE *BRASSICA OLERACEA* PLANT AND METHOD FOR PRODUCING SAME

CROSS-REFERENCE TO RELATED APPLICATIONS

This application claims priority from Japanese Patent Application No. 2018-030872 (date of filing: Feb. 23, 2018), the entire disclosure of which is incorporated herein by reference.

TECHNICAL FIELD

The present invention relates to a *Brassica oleracea* plant to which self-compatibility (SC) has been imparted. More particularly, the present invention relates to a technology for overcoming problems in seed production by introducing a loss-of-function gene locus in place of a self-incompatibility (SI) gene, inherently possessed by a *Brassica oleracea*.

BACKGROUND ART

Plants of the family Brassicaceae originated from the Middle East and the Mediterranean coast and include extremely important agricultural crops of the genus *Brassica*. In particular, *Brassica oleracea* is an extremely important plant species including *B. oleracea* var. *capitata* (cabbage), *B. oleracea* var. *italica* (broccoli), *B. oleracea* var. *botrytis* (cauliflower), *B. oleracea* var. *gemmifera* (Brussels sprout), *B. oleracea* var. *gongyloides* (kohlrabi), *B. oleracea* var. *acephara* (ornamental cabbage, kale), *B. oleracea* var. *albograbra* (Chinese kale), along with others.

Many plants of the family Brassicaceae, including *Brassica oleracea*, possess "self-incompatibility", in which if a plant is subjected to pollination by another plant having the same S haplotype as the plant itself, pollen germination on the stigma and pollen tube growth are inhibited, and the plant will not be fertilized. For crops in the family Brassicacaea, large-scale seed production providing first filial generation (F1) varieties has been established since the 1960s, and the development of F1 varieties has been actively carried out by various varietal development companies. Since F1 varieties that inherit the excellent properties of their parents have high uniformity amongst the varieties compared to native varieties and open pollinated varieties, and exhibit high ability to adapt to various environments, these varieties have high commercial utility value and have been utilized in many countries.

Regarding the specific method for producing F1 seeds, a parental line having a certain S haplotype and a parental line having another S haplotype are cultivated in the same farm field, and cross pollination by entomophily, utilizing honeybees and the like, is carried out. In this process, self pollen and pollen from the same parental line are also pollinated on a plant; however, since germination and pollen tube growth from such pollen is inhibited due to the property of SI, self-propagated seeds (self seeds) are, theoretically, not formed. On the other hand, when pollen from a line having a different S haplotype is pollinated on a plant, normal fertilization occurs, leading to the formation of F1 seeds.

As such, SI inherently possessed by plants has high utility value for an F1 seed production system. However, there is also a problem in this scenario.

With regard to SI, which is a biological phenomenon, expression of the function is not perfect and the intensity of SI varies depending on the genetic background, the type of S haplotype, and environmental factors. Consequently, there is a problem that self-propagated seeds produced by self-fertilization make up a proportion of the harvest due to insufficient inhibition of pollen tube growth of self pollen.

In order to solve this problem, breeders have hitherto selected lines that strongly express the function of SI amongst the many S haplotypes existing in *Brassica oleracea*. In spite of this, in the case in which seed production has been carried out at a large-scale commercial level, incorporation of self-propagated seeds cannot be completely avoided.

In the case in which such self-propagated seeds are included in a commercial product supplied as an F1 seed, there is also the problem that not only the value of the seed crop is lowered, but also parental lines that are important to varietal development companies become available to competitors.

At the beginning of the 1990s, a means for solving the above-described problems in F1 seed production came to be achieved by utilizing cytoplasmic male sterility (CMS). CMS is a maternally inherited trait in the cytoplasmic genome having a causative gene that induces male sterility (non-functional pollen). Depending on the crop, there are species with unstable expression of this sterility trait; however, since the CMS of *Brassica oleracea* is very stable and it is not easily affected by the environment, high-purity F1 seed production has been enabled.

Unfortunately, the SI that is inherently possessed by crops in the family Brassicaceae is persistent, and this trait remains as a troublesome property in the propagation of the parental lines (stock seed propagation) used to accomplish F1 seed production.

This is because the property of SI has become completely unnecessary in the F1 seed production system utilizing CMS; however, since all parental lines have SI, even if ordinary mating is carried out, self-fertilization rarely occurs and stock seed propagation cannot be carried out efficiently. Furthermore, in the case in which at the time of F1 seed production, the parental lines have the same S haplotype, there is a problem that F1 seeds from this combination cannot be produced.

Various studies have been conducted on the technique for breaking down self-incompatibility. For example, stock seed propagation has been attempted by: (i) the technique of performing bud pollination by hand mating, (ii) the technique of exposing blooming flowers to $CO_2$, or (iii) the technique of performing an operation such as spraying an aqueous solution of NaCl on flowers (T. Guohua et al., Cruciferae Newsletter (1986) p75 (Non Patent Document 1)).

However, there remains the problem that since bud pollination by hand mating takes time and labor, it is difficult to perform large-scale production, while with a $CO_2$ treatment or a NaCl treatment, the effect of breaking down SI is not always stable, depending on the genetic background and the S haplotype of various lines. Thus, the situation which all varietal development companies struggle with, stock seed propagation, continues (Niikura et al., Theor Appl Genet (2000) vol. 101 p1189 (Non Patent Document 2)).

Regarding relevant prior art technologies, for example, in JP 4346933 B2 (Patent Document 1), an S genotype identification method for plants of the family Brassicaceae is described. Furthermore, in WO 2014/115680 A (Patent Document 2), a method for creating a plant of the family Brassicaceae having self-compatibility is described. However, the object to which the method is directed in this Document is *Brassica rapa*, which is a plant of the genus

*Brassica*, but it is completely different from *Brassica oleracea*. It is well known to those ordinarily skilled in the art that even if the "genus" of plants is the same, when the "species" is different, any knowledge related to one "species" cannot be directly applied to another "species".

Thus, regarding the F1 seed production system for *Brassica oleracea* utilizing CMS, a method of propagating a stock seed efficiently and stably is not reported.

PRIOR ART LIST

Patent Document

Patent Document 1: Japanese Patent Publication No. 4346933 B2 (JP 4346933 B2)
Patent Document 2: WO 2014/115680 A Non Patent Document Non Patent Document 1: Cruciferae Newsletter (1986) p75 T. Guohua et al., "Use of CO2 and salt solution to overcome self-incompatibility of Chinese cabbage (*B. campestris* spp. *Pekinensis*)."
Non Patent Document 2: Theor Appl Genet (2000) vol. 101 p1189 S. Niikura et al., "Genetic analysis of the reaction level of self-incompatibility to a 4% CO2 gas treatment in the radish (*Raphanus sativus* L.)."
Non Patent Document 3: Breeding Science (2003) vol. 53 p199 M. Watanabe et al., "Recent progress on self-incompatibility research in *Brassica* species."
Non Patent Document 4: Theor Appl Genet (1996) vol. 92 p388, T. Nishio et al., "Registration of S alleles in *Brassica campestris* L by the restriction fragment sizes of SLGs."
Non Patent Document 5: Breeding Science (2004) vol. 54 p291 A. Horisaki et al., "Effectiveness of insect-pollination to evaluate the level of self-incompatibility and genetic variation in *Brassica rapa* L."
Non Patent Document 6: Proc Natl Acad Sci (1997) vol. 94 p7673 M. Kusaba et al., "Striking sequence similarity in inter- and intra-specific comparisons of class I SLG alleles from *Brassica oleracea* and *Brassica campestris*: Implications for the evolution and recognition mechanism."
Non Patent Document 7: Plant Cell (2007) vol. 19 p3961 M. Kitaura et al., "Two distinct forms of M-locus protein kinase localize to the plasma membrane and interact directly with S-locus receptor kinase to transduce self-incompatibility signaling in *Brassica* raps."
Non Patent Document 8: Plant Cell (2012) vol. 24 p4607 E. Indriolo et al., "The ARC1 E3 ligase gene is frequently deleted in self-compatible Brassicaceae species and has a conserved role in *Arabidopsis lyrata* self-pollen rejection."

SUMMARY OF THE INVENTION

Problems to be Solved by the Invention

It is an object of the present invention to provide technical means enabling stable and efficient stock seed production for *Brassica oleracea* plants. Furthermore, it is another object of the present invention to establish a technology enabling F1 seed production for *Brassica oleracea* plants using any parental lines, without having to consider the S haplotypes of the parental lines.

Means for Solving Problems

The inventors of the present invention have hitherto repeatedly conducted a thorough investigation in order to develop a technology enabling stable and efficient stock seed production for *Brassica oleracea* plants. From numerous investigations, the present inventors studied the self-incompatibility inherently possessed by *Brassica oleracea* plants.

The present inventors speculated that if a self-compatibility gene deficient in the function of self-incompatibility can be found, self-mating or mating with the same S haplotype is enabled, and thus, not only stock seed propagation can be efficiently achieved without any special treatment, but F1 seed production between parental lines having the same S haplotype is also enabled.

Regarding a specific method of utilizing a self-compatible line, for example, when a paper bag for mating is put on the inflorescence where flowers have bloomed and physical impacts such as tapping the bag with a hand are applied, the pollen of the plant itself adheres to the stigma and fertilization occurs. Even in the case of performing seed production on a large scale, self-fertilized seeds can be obtained efficiently and in large quantities by insect pollination with honeybees and the like.

Despite such high commercial merits, such a method has not been utilized for important *Brassica oleracea* plants such as broccoli and cabbages because genetic resources for self-compatibility do not exist in these crops.

The inventors of the present invention conducted extensive investigations on the genetic resources of *Brassica oleracea* species and related species thereof, and repeatedly conducted a thorough investigation by DNA analysis of S haplotypes and mating tests. As a result of various investigations and studies accompanied by enormous efforts, the inventors found that among the genetic resources possessed by SAKATA SEED CORPORATION, Chinese kale "K-3" line, *Brassica oleracea* wild species "T-16" line, and cauliflower "CF-33" line have the property of self-compatibility.

Chinese kale, *Brassica oleracea* wild species, and cauliflower are related species of broccoli and cabbage. However, since these have a large number of traits considered undesirable for the target crops, it is difficult to utilize the above-mentioned species as breeding materials. Particularly in these species, since there are a large number of factors affecting the phenotype in the region of the S locus, it is often impossible to efficiently develop parental lines by simply proceeding with backcrossing (BC).

Thus the inventors of the present invention conducted a genetic analysis of the region of the S-alleles, and succeeded in breeding high-quality broccoli and cabbage, into which self-compatibility has been introduced, using backcrossing in a large-scale population.

As such, the inventors of the present invention found a *Brassica oleracea* line having self-compatibility and demonstrated that a breeding line having high industrial utility value can be developed. Further, development of a novel self-compatible line is enabled by utilizing the self-compatible *Brassica oleracea* plant according to the present invention or a method for developing a self-compatible line, and when this is utilized, stable production of stock seed can be accomplished. Furthermore, by utilizing a parental line developed as such, it is possible to develop novel combinations of F1 varieties without considering the S haplotype of the partner parent.

The present invention is based on these findings.

That is, according to the present invention, the following inventions are provided.

<1> A *Brassica oleracea* plant having self-compatibility, or a progeny thereof, wherein the plant excludes cauliflower and Chinese kale.

<2> The *Brassica oleracea* plant having self-compatibility according to the above item <1>, or a progeny thereof, wherein the plant excludes cauliflower and Chinese kale, comprising;

a gene residing at the S locus of a self-compatible *Brassica oleracea* plant which substituted with a gene residing at a self-incompatibility gene locus (S locus) of a self-incompatible *Brassica oleracea* plant excluding cauliflower and Chinese kale.

<3> The *Brassica oleracea* plant having self-compatibility according to the above item <1> or <2>, or a progeny thereof, which is obtainable by mating a self-compatible *Brassica oleracea* plant with a self-incompatible *Brassica oleracea* plant excluding cauliflower and Chinese kale and selecting an individual having self-compatibility from the cross-progeny.

<4> The self-compatible *Brassica oleracea* plant according to any one of the above items <1> to <3>, having any one or more DNAs selected from the group consisting of the following (a) to (c) in the S locus:

(a) a DNA including a nucleotide sequence set forth in SEQ ID NO:1 or SEQ ID NO:2;

(b) a DNA including a nucleotide sequence having a sequence identity of 95% or higher with a nucleotide sequence set forth in SEQ ID NO:1 or SEQ ID NO:2, the DNA being involved in the expression of self-compatibility in a plant; or (c) a DNA including a nucleotide sequence obtained by deletion, substitution, insertion, and/or addition of one or a plurality of bases in a nucleotide sequence set forth in SEQ ID NO:1 or SEQ ID NO:2, the DNA being involved in the expression of self-compatibility in a plant.

<5> The *Brassica oleracea* plant according to the above item <4>, or a progeny thereof, wherein the plant is self-compatible with an S allele including a DNA of any one of the above-described items (a) to (c) introduced into a self-incompatibility gene locus.

<6> The self-compatible *Brassica oleracea* plant according to any one of the above items <1> to <5>, or a progeny thereof, wherein the plant is broccoli or cabbage.

<7> A *Brassica oleracea* plant excluding Chinese kale, or a progeny thereof, wherein the plant has a self-compatibility gene locus "BoS-SC1" in S-locus, and the gene locus "BoS-SC1" is found in the Chinese kale variety identified by Accession No. FERM BP-22347.

<8> A *Brassica oleracea* plant excluding Chinese kale, or a progeny thereof, wherein the plant has a self-compatibility gene locus "BoS-SC1" in S-locus, and the gene locus "BoS-SC1" is found in the broccoli variety identified by Accession No. FERM BP-22347.

<9> The *Brassica oleracea* plant excluding Chinese kale according to the above item <7> or <8>, or a progeny thereof, wherein the gene locus "BoS-SC1" includes a nucleotide sequence of the following (i) to (iii):

(i) a nucleotide sequence set forth in SEQ ID NO:1;

(ii) a nucleotide sequence having a sequence identity of 95% or higher with a nucleotide sequence set forth in SEQ ID NO:1; or (iii) a nucleotide sequence obtained by deletion, substitution, insertion, and/or addition of one or a plurality of bases in a nucleotide sequence set forth in SEQ ID NO:1.

<10> The *Brassica oleracea* plant according to any one of the above items <7> to <9>, or a progeny thereof, wherein the plant is broccoli or cabbage.

<11> A *Brassica oleracea* plant excluding cauliflower and *Brassica oleracea* wild species, or a progeny thereof, wherein the plant has a self-compatibility gene locus "BoS-SC2" in S locus, and the gene locus "BoS-SC2" is found in the cauliflower variety identified by Accession No. FERM BP-22350.

<12> A *Brassica oleracea* plant excluding cauliflower and *Brassica oleracea* wild species, or a progeny thereof, wherein the plant has a self-compatibility gene locus "BoS-SC2" in S locus, and the gene locus "BoS-SC2" found in the broccoli variety identified by Accession No. FERM BP-22348.

<13> The *Brassica oleracea* plant excluding cauliflower and a *Brassica oleracea* wild species according to the above item <11> or <12>, or a progeny thereof, wherein the gene locus "BoS-SC2" includes a nucleotide sequence of the following (I) to (III):

(I) a nucleotide sequence set forth in SEQ ID NO:2;

(II) a nucleotide sequence having a sequence identity of 95% or higher with a nucleotide sequence set forth in SEQ ID NO:2; or (III) a nucleotide sequence obtained by deletion, substitution, insertion, and/or addition of one or a plurality of bases in a nucleotide sequence set forth in SEQ ID NO:2.

<14> The *Brassica oleracea* plant according to any one of the above items <11> to <13>, or a progeny thereof, wherein the plant is broccoli or cabbage.

<15> Broccoli identified by Accession No. FERM BP-22349, or a progeny thereof.

<16> Broccoli identified by Accession No. FERM BP-22348, or a progeny thereof.

<17> A part of a plant body of the plant according to any one of the above items <1> to <16> or a progeny thereof.

<18> A seed of the plant according to any one of the above items <1> to <16> or a progeny thereof.

<19> A method for developing a *Brassica oleracea* plant having self-compatibility, wherein the plant excludes cauliflower and Chinese kale, the method including mating a self-compatible *Brassica oleracea* plant with a self-incompatible *Brassica oleracea* plant excluding cauliflower and Chinese kale and selecting an individual having self-compatibility from a cross-progeny.

<20> The method for developing a self-compatible *Brassica oleracea* plant according to the above item <19>, wherein the self-compatibility of the self-compatible *Brassica oleracea* plant is associated with a gene residing at a self-incompatibility gene locus (S locus).

<21> The method for developing a self-compatible *Brassica oleracea* plant according to the above item <19> or <20>, wherein the self-compatible *Brassica oleracea* plant has any one or more DNAs selected from the group consisting of the following (a) to (c) in the S locus:

(a) a DNA including a nucleotide sequence set forth in SEQ ID NO:1 or SEQ ID NO:2;

(b) a DNA including a nucleotide sequence having a sequence identity of 95% or higher with a nucleotide sequence set forth in SEQ ID NO:1 or SEQ ID NO:2, the DNA being involved in the expression of self-compatibility in a plant; or (c) a DNA including a nucleotide sequence obtained by deletion, substitution, insertion, and/or addition of one or a plurality of bases in a nucleotide sequence set forth in SEQ ID NO:1 or SEQ ID NO:2, the DNA being involved in the expression of self-compatibility in a plant.

<22> The method for developing a self-compatible *Brassica oleracea* plant according to any one of the above items <19> to <21>, wherein the selection of a self-compatible individual from the cross-progeny includes selecting a self-compatible plant based on whether the individual has the DNA of any one of (a) to (c) according to the above item <21>, as an indicator.

<23> The method for developing a self-compatible *Brassica oleracea* plant according to any one of the above items <19> to <22>, the method further including distinguishing the genotype using a DNA marker located in a region in the extreme vicinity of the S locus (0 to 4 cM from the S locus) including a gene associated with self-compatibility, and selecting an individual having self-compatibility.

<24> The method for developing a self-compatible *Brassica oleracea* plant according to any one of the above items <19> to <23>, the method including performing continuous backcrossing using the self-incompatible *Brassica oleracea* plant excluding cauliflower and Chinese kale as a parental line for backcrossing.

<25> The method for growing a self-compatible *Brassica oleracea* plant according to any one of the above items <19> to <24>, wherein the self-compatible *Brassica oleracea* plant used in the mating is the Chinese kale variety identified by Accession No. FERM BP-22347, the broccoli variety identified by Accession No. FERM BP-22349, the broccoli variety identified by Accession No. FERM BP-22348, or the cauliflower variety identified by Accession No. FERM BP-22350.

<26> The method for developing a self-compatible *Brassica oleracea* plant according to any one of the above items <19> to <25>, wherein the self-incompatible *Brassica oleracea* plant is broccoli or cabbage.

<27> A marker for detecting self-compatibility in a *Brassica oleracea* plant, the marker including a nucleotide sequence of any one of the following (A) to (C):

(A) a nucleotide sequence set forth in SEQ ID NO:1 or SEQ ID NO:2;

(B) a nucleotide sequence having a sequence identity of 95% or higher with a nucleotide sequence set forth in SEQ ID NO:1 or SEQ ID NO:2; or (C) a nucleotide sequence obtained by deletion, substitution, insertion, and/or addition of one or a plurality of bases in a nucleotide sequence set forth in SEQ ID NO:1 or SEQ ID NO:2.

<28> A method for producing seeds of a *Brassica oleracea* plant, the method including self-propagating a self-compatible *Brassica oleracea* plant obtained by the development method according to any one of the above items <19> to <26>, or a progeny thereof, and thereby producing seeds thereof.

<29> A method for maintaining or propagating a parental line of a useful first filial generation line using the development method according to any one of the above items <19> to <26>.

<30> A marker for performing a genotype analysis of a region in the vicinity of an S locus of a *Brassica oleracea* plant, the region having any one or more of nucleotide sequences set forth in SEQ ID NO:10 to SEQ ID NO:15.

<31> A method for producing first filial generation seeds of *Brassica oleracea* by utilizing cytoplasmic male sterility (CMS), the method including:

a step of propagating a parental line of a first filial generation line by utilizing a *Brassica oleracea* plant having self-compatibility.

<32> The method for producing seeds according to the above item <31>, wherein the *Brassica oleracea* plant having self-compatibility has any one or more DNAs selected from the group consisting of the following (a) to (c) in the S locus:

(a) a DNA including a nucleotide sequence set forth in SEQ ID NO:1 or SEQ ID NO:2;

(b) a DNA including a nucleotide sequence having a sequence identity of 95% or higher with a nucleotide sequence set forth in SEQ ID NO:1 or SEQ ID NO:2, the DNA being involved in the expression of self-compatibility in a plant; or (c) a DNA including a nucleotide sequence obtained by deletion, substitution, insertion, and/or addition of one or a plurality of bases in a nucleotide sequence set forth in SEQ ID NO:1 or SEQ ID NO:2, the DNA being involved in the expression of self-compatibility in a plant.

<33> The method for producing seeds according to the above item <31> or <32>, wherein the *Brassica oleracea* plant having self-compatibility is any one of the following 1) to 6):

1) a *Brassica oleracea* plant excluding Chinese kale, wherein the plant has a self-compatibility gene locus "BoS-SC1" in the S locus, and the gene locus "BoS-SC1" is found in the Chinese kale variety identified by Accession No. FERM BP-22347;

2) a *Brassica oleracea* plant excluding Chinese kale, wherein the plant has a self-compatibility gene locus "BoS-SC1" in the S locus, and the gene locus "BoS-SC1" is found in the broccoli variety identified by Accession No. FERM BP-22349;

3) a *Brassica oleracea* plant excluding cauliflower and *Brassica oleracea* wild species, wherein the plant has a self-compatibility gene locus "BoS-SC2" in the S locus, and the gene locus "BoS-SC2" is found in the cauliflower variety identified by Accession No. FERM BP-22350;

4) a *Brassica oleracea* plant excluding cauliflower and *Brassica oleracea* wild species, wherein the plant has a self-compatibility gene locus "BoS-SC2" in the S locus, and the gene locus BoS-SC2" is found in the broccoli variety identified by Accession No. FERM BP-22348;

5) broccoli identified by Accession No. FERM BP-22349, or a progeny thereof; and 6) broccoli identified by Accession No. FERM BP-22348, or a progeny thereof.

Effects of the Invention

When the *Brassica oleracea* plant having self-compatibility according to the present invention is utilized, development of a new *Brassica oleracea* parental line having excellent seed production properties is enabled. By utilizing a self-compatible line created as such, stock seed propagation of a parental line for producing F1 seeds is achieved efficiently. For this reason, the current efforts needed for conventionally self-propagation can be decreased to a large extent, and the cultivation area of the seed production farm field can be reduced. Furthermore, such a self-compatible line thus created is expected to greatly contribute even from the viewpoint of stable supply of stock seeds, which has often been a problem for conventional SI lines.

Furthermore, when a line developed as such is utilized, novel combinations of F1 varieties can be developed without concern for the S haplotype of the seed production parents for F1 seed production. This widens the range of F1 varieties, which leads to extension of the possibility of breeding itself.

BRIEF DESCRIPTION OF DRAWINGS

FIGS. 1A-1C show the plant shapes of broccoli (potted cultivation) of various generations in Example 2. Among the diagrams, FIG. 1A shows the plant shape of "BR-9", which is an elite line of the SI system used for backcrossing, FIG. 1B shows the plant shape of an intermediate stage of backcrossing, and FIG. 1C shows the plant shape of "SC-BR-9", which is an SC line in which BC has proceeded so far as to acquire a plant shape similar to BR-9.

FIG. 2A shows "BR-9", which is an elite line of the SI system used for backcrossing, FIG. 2B shows "SC-BR-9", which is an SC line in which BC has proceeded so far as to acquire a plant shape similar to "BR-9", and FIG. 2C shows the plant shape of "CMS-SC-BR-9", which is a line in which "SC-BR-9" has been substituted with CMS cytoplasm.

FIG. 5C shows the results of counting the numbers of seeds formed in various pods in Example 6.

EMBODIMENTS OF THE INVENTION

Figure 2A:
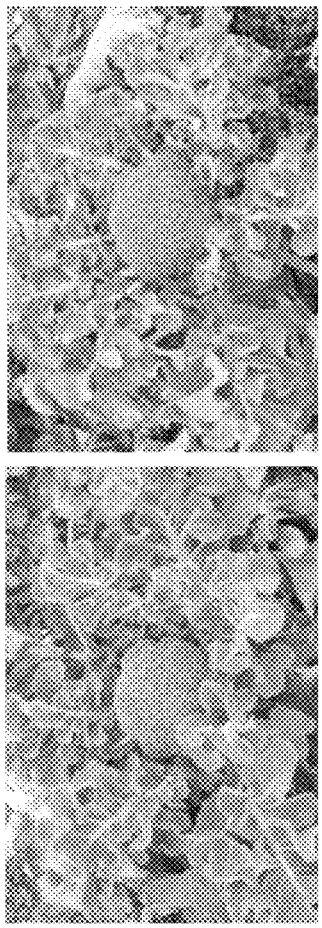
FIGS. 2A-2C show broccoli (cultivation in farm field) developed in Example 2. Among the diagrams.

The present invention will be described in detail below.
Self-Compatible *Brassica oleracea* Plant and Method for Growing Same The present invention relates, as described above, to a *Brassica oleracea* plant (excluding cauliflower and Chinese kale) having self-compatibility, or a progeny thereof.

Here, the *Brassica oleracea* plant having self-compatibility is obtained by substituting a gene residing at a self-incompatibility gene locus (S locus) of a self-incompatible *Brassica oleracea* plant (excluding cauliflower and Chinese kale) with a gene residing at the S locus of a self-compatible *Brassica oleracea* plant. That is, the self-compatible *Brassica oleracea* according to the present invention refers to a *Brassica oleracea* plant (excluding cauliflower and Chinese kale) having self-incompatibility converted to self-compatibility by substituting a gene residing at the S locus of a self-incompatible *Brassica oleracea* plant (excluding cauliflower and Chinese kale) with a gene residing at the S locus of another *Brassica oleracea* plant having self-compatibility.

Here, the phrase "substituted with" means that a gene expressing the trait of self-incompatibility is substituted with a gene capable of expressing self-compatibility, and the means for substituting is not particularly limited.

The *Brassica oleracea* plant having self-compatibility (self-compatible *Brassica oleracea* plant) according to the present invention is deficient in a self-incompatibility function that is inherently possessed by an S gene, and it is made possible to develop a novel *Brassica oleracea* plant having self-compatibility using the above-mentioned plant as a genetic resource. In other words, the self-compatible *Brassica oleracea* plant according to the present invention has been made self-compatible by introducing an S allele including a self-compatibility factor found from a self-compatible *Brassica oleracea* plant into a self-incompatibility gene locus, and includes progenies thereof.

Here, the technique for determining whether a "self-compatible *Brassica oleracea* plant" has "self-compatibility" is not particularly limited and may be determined by any known technique; however, for example, it can be determined by, adopting the techniques for selecting a self-compatible plant described in the present specification, for example, a mating test by self-pollination, a mating test on the occasion of introducing the S haplotype as will be described below, comparison of the seed set percentages of open flower pollination and bud pollination as will be described below, utilization of a DNA marker related to a known S locus, and the like. Specifically, for example, whether a plant has self-compatibility or not can be determined by adopting the technique described in Example 1 that will be described below.

According to the present invention, a "*Brassica oleracea* plant" is a plant of the family Brassicaceae and means a plant of the *Brassica oleracea* species among plants of the genus *Brassica*, and examples thereof include *B. oleracea* var. *capitata* (cabbage), *B. oleracea* var. italics (broccoli), *B. oleracea* var. *botrytis* (cauliflower), *B. oleracea* var. gemmifera (Brussels sprout), *B. oleracea* var. gongyloides (kohlrabi), *B. oleracea* var. acephara (ornamental cabbage, kale), and *B. oleracea* var. albograbra (Chinese kale).

Furthermore, the "self-compatibility" (SC) refers to a property in which the function of self-incompatibility (SI) inherently possessed by a *Brassica oleracea* plant is deficient, and which enables fertilization of the plant by itself or by a plant having an S haplotype of the same type as the plant itself.

The self-compatible *Brassica oleracea* plant according to the present invention typically has the following features.

(1) Since the function of self-incompatibility is deficient, efficient mating with the plant itself or with a plant having the same S haplotype as the plant itself is enabled, and propagation of stock seeds, which has been conventionally difficult, can be efficiently carried out.

(2) Specifically, the plant is a plant having a DNA sequence set forth in SEQ ID NO:1 or SEQ ID NO:2 in the S locus, and is a plant exhibiting self-compatibility by having that allele.

(3) By utilizing a line having the above-described sequence as a mating material, developing a novel parental line having self-compatibility is enabled.

Production Method

According to the present invention, when a self-incompatible *Brassica oleracea* plant is mated with a *Brassica oleracea* plant that has been found to have self-compatibility, and an individual having self-compatibility is selected from the cross-progeny, a plant obtained by imparting self-compatibility to a self-incompatible *Brassica oleracea* plant can be produced.

That is, a method for developing a *Brassica oleracea* plant having self-compatibility according to the present invention includes, as described above, mating a self-compatible *Brassica oleracea* plant with a self-incompatible

*Brassica oleracea* plant (excluding cauliflower and Chinese kale) and selecting an individual having self-compatibility from the cross-progeny.

The "self-compatible *Brassica oleracea* plant" used herein as a genetic resource is a *Brassica oleracea* plant having a self-compatibility factor, and in a mating test by self-pollination, a *Brassica oleracea* plant having a self-compatibility factor can be selected by adopting a mating test at the time of S haplotype introduction as will be described below, comparison of the seed set percentages of open flower pollination and bud pollination as will be described below, utilization of a DNA marker related to a known S locus, and the like. Specifically, for example, it is possible to select a *Brassica oleracea* plant having a self-compatibility factor by adopting the technique described in Example 1 that will be described below.

Furthermore, the "self-compatibility" of the self-compatible *Brassica oleracea* plant is a property associated with a gene residing at a self-incompatibility gene locus (S locus). That is, according to the present invention, the "self-compatibility" refers to self-compatibility expressed due to a function of a gene residing at the S locus or deficiency of that function (or is presumed to be so), or due to the influence of a gene residing at the S locus, and for example, acquisition of self-compatibility due to an effect other than the S locus is excluded. Incidentally, regarding *Brassica oleracea* plants, as will be described below in Example 1, according to conventional knowledge, it is considered that in a majority of cases, even plants having the property of SI may appear to have SC due to an effect other than the S locus (Horisaki et al., 2004 (Non Patent Document 5)).

According to the present invention, the "self-compatible *Brassica oleracea* plant" used as a material has a DNA of any one of the following items (a) to (c) in the S locus:

(a) a DNA including a nucleotide sequence set forth in SEQ ID NO:1 or SEQ ID NO:2, (b) a DNA including a nucleotide sequence having a sequence identity of 95% or higher with a nucleotide sequence set forth in SEQ ID NO:1 or SEQ ID NO:2, the DNA being involved in the expression of self-compatibility in a plant, or (c) a DNA including a nucleotide sequence obtained by deletion, substitution, insertion, and/or addition of one or a plurality of bases in a nucleotide sequence set forth in SEQ ID NO:1 or SEQ ID NO:2, the DNA being involved in the expression of self-compatibility in a plant.

Here, the term "having" in the case of "having a DNA" may be replaced with "including"; however, the term may be replaced preferably with "consisting substantially of", and more preferably with "consisting of".

Furthermore, with regard to the above-described (b), in a case in which it is said to "have a sequence identity of 95% or higher with a nucleotide sequence set forth in SEQ ID NO:1 or SEQ ID NO:2", when the sequence identity is calculated using a nucleotide sequence set forth in SEQ ID NO:1 or SEQ ID NO:2 and a known algorithm for homology search (for example, using default parameters, that is, parameters of initial settings, are used), such as BLAST or FASTA, a DNA having a sequence identity of at least 95%, preferably at least 96%, more preferably at least 97%, even more preferably at least 98%, and particularly preferably at least 99%, is included.

Here, regarding the term "sequence identity", for example, when two base (nucleotide) sequences are subjected to alignment (provided that gaps may be introduced, or gaps may not be introduced), the term refers to the proportion (%) of the number of identical bases with respect to the total number of bases including gaps.

Furthermore, herein, when it is said that the DNA of (b) is "involved in the expression of self-compatibility in a plant", it is implied that by the DNA of (b), a plant having it in the S locus substantially expresses self-compatibility.

Furthermore, with regard to the above-described (c), the term "a plurality" as used in the phrase "a nucleotide sequence obtained by deletion, substitution, insertion, and/or addition of one or a plurality of bases in a nucleotide sequence set forth in SEQ ID NO:1 or SEQ ID NO:2" means, for example, about 10 bases, preferably about 7 bases, preferably 5 bases, and more preferably 3 bases.

According to one preferred embodiment of the present invention, in the method of the present invention, the "self-compatible *Brassica oleracea* plant" as a material is the Chinese kale variety identified by Accession No. FERM BP-22347, the broccoli variety identified by Accession No. FERM BP-22349, the broccoli variety identified by Accession No. FERM BP-22348, or the cauliflower variety identified by Accession No. FERM BP-22350.

Furthermore, the "self-incompatible *Brassica oleracea* plant" used as a material herein is not particularly limited as long as the plant can be mated with the "self-compatible *Brassica oleracea* plant" used as the above-described material and has self-incompatibility inherently possessed by a plant of the family Brassicaceae. However, with regard to cauliflower and Chinese kale, since those having self-compatibility have already been known, cauliflower and Chinese kale are excluded from the "self-incompatible *Brassica oleracea* plant" used as a material. The "self-incompatible *Brassica oleracea* plant" is preferably broccoli, cabbage, Brussels sprout, kohlrabi, ornamental cabbage, or kale, and more preferably broccoli or cabbage.

In the development method of the present invention, first, a self-compatible *Brassica oleracea* plant is mated with a self-incompatible *Brassica oleracea* plant (excluding cauliflower and Chinese kale). Then, an individual having self-compatibility is selected from the cross-progeny obtainable by mating.

That is, an S haplotype of the S locus of the "self-compatible *Brassica oleracea* plant" as a material is introduced into a self-incompatible *Brassica oleracea* plant (excluding cauliflower and Chinese kale), and an individual that has self-compatibility with the S haplotype introduced therein is selected from the cross-progeny.

Here, mating is not particularly limited as long as a cross-progeny is obtained by mating "a self-compatible *Brassica oleracea* plant" and "a self-incompatible *Brassica oleracea* plant" as materials, and the mating may be any of natural mating such as entomophily, hand mating, and the like. Furthermore, the mating as used herein has a meaning that also includes backcrossing.

On the occasion of introducing an S haplotype, it is possible to check whether the plant is self-compatible or self-incompatible by a mating test.

Specifically, a mating test by self-pollination and a mating test by cross-pollination using the pollen of a line having a different S haplotype as an object of comparison are carried out. The results of self-pollination and cross-pollination are compared, and in the case in which seeds have been successfully produced to the same extent, it is considered to be self-compatible, while in a case in which the seed set percentage of self-pollination is low, it is considered to be self-incompatible.

Furthermore, generally, since SI is a response in bloomed flowers, so it can be determined which property between SI and SC will be exhibited by the plant by comparing the seed set of open flower pollination (OFP) and bud pollination (BP). In a bud stage, since the expression of an SI gene is low, when the calyxes and the petals are stripped and then pollination is forcibly achieved (bud pollination), it is possible to circumvent SI and form seeds as long as egg cells are in a state of having an ability for fertilization. In the case in which the seed set percentage for OFP mating is lower than the seed set percentage for BP mating, the plant can be considered to be of an SI line using the principle described above.

According to the present invention, for an analysis of the S haplotype, the S haplotype can be classified by taking the polymorphism of a group of genes residing at the S locus as described in the document by Watanabe et al. (2003) (Non Patent Document 3) (S-receptor kinase; SRK, S-locus glycoprotein; SLG, S locus protein 11; SP11 (=S locus cysteine-rich protein; SCR)) as an indicator. The means for classification of the S haplotype may be any arbitrary method, and for example, it is possible to use PCR primers that are generally known, such as described in the document by Nishio et al. (1996) (Non Patent Document 4), or the like. Furthermore, an analysis in which a DNA marker based on SEQ ID NO:1 or SEQ ID NO:2 is produced, or an analysis of the nucleotide sequence of an S gene may be carried out.

Therefore, according to a preferred embodiment of the present invention, regarding the selection of a self-compatible individual from the cross-progeny, a self-compatible plant can be selected on the basis of whether an individual has a DNA of any one of the above-described items (a) to (c), as an indicator. That is, when an individual has a DNA of any one of the above-described items (a) to (c), the individual exhibits self-compatibility.

As such, according to the present invention, in the determination of self-compatibility, the presence or absence of a self-compatibility gene locus can be distinguished even when the S locus is in a heterozygous state, by performing an analysis of the S locus using a DNA marker, and more efficient backcrossing can be carried out than a mating test.

Therefore, according to a preferred embodiment of the present invention, the breeding method of the present invention includes performing repeated backcrossing using the above-described self-incompatible *Brassica oleracea* plant (excluding cauliflower and Chinese kale) as the parental line for backcrossing.

In the process of performing backcrossing, unless special selection is carried out, the averages of the genome substitution ratio in the population of various generations are 75% for the first generation (BC1F1), 87.5% for the second generation (BC2F1), 93.75% for the third generation (BC3F1), and 96.875% for the fourth generation (BC4F1). Thus, as generations pass on, the population acquires a genotype closer to the parental line for backcrossing (the recurrent parent). Therefore, in order to create practically useful near-isogenic lines having only the S locus substituted from the parental line for backcrossing, generally, backcrossing for 6 or 7 times is required.

In order to more efficiently proceed with backcrossing that requires a long time period as such, it is also possible to bring regions other than the S locus close to the parental line for backcrossing earlier by using genome-wide DNA markers.

For example, as described above, in the first generation of backcrossing (BC1F1), 75% on the average of the genome has the same genotype as the recurrent parent. Because the BC1F1 generation is a segregating generation, the genome substitution ratios possessed by individuals are different. When the scale of the population is expanded, depending on the individuals, it is also possible to acquire an individual in which 90% or more of the genome regions exhibit the same genotype as the recurrent parent. By selecting such an individual, regions other than the S locus can be matched to have the same genotype as the recurrent parent, in an early stage using a smaller number of generations.

Regarding a specific means that can be utilized as a genome-wide DNA marker, in the case of having the genomic sequence information of the recurrent parent, a DNA marker based on that information is produced, and then genotyping of various gene loci may be carried out.

Furthermore, even in a case in which the genomic sequence information of the recurrent parent is not available, it is possible to select an individual having a genotype close to the recurrent parent from the segregating generation by utilizing a random PCR method such as a random amplified polymorphic DNA (RAPD) method, a sequence-related amplified polymorphism (SRAP) method, or an amplified fragment length polymorphism (AFLP) method. In addition to that, if there is a single nucleotide polymorphism (SNP) genotyping chip designed to comprehensively analyze a large number of SNPs scattered in the genome (a product manufactured by Affymetrix, Inc. or a product manufactured by Illumina, Inc.), an analysis may be carried out using such a means.

As another point to be noted at the time of backcrossing, linkage drag of a non-target trait linked to the S locus may be mentioned.

In conventional backcrossing, substitution of a region other than chromosome 6 where an S gene resides is substituted with the genotype of the recurrent parent can be carried out relatively easily when generations are repeated, although it takes time as described above. On the other hand, with regard to a region in the vicinity of the S locus, a breeding program that intentionally excludes this region is needed.

As a specific example, a marker residing in the vicinity of the S locus is designed, and the genotype of individuals together with a marker for distinguishing the S locus in a segregating generation can be analyzed. In most cases, the two markers are co-segregated (linked); however, extremely rarely the linkage between the two markers is broken, and there appears an individual in which the S gene has a gene locus of the self-compatibility line, while the genomic region in the vicinity thereof exhibits a genotype of the parental line for backcrossing. By selecting such an individual it is possible to select an individual from which a non-target trait linked to the S locus has been removed.

The DNA sequence information in the region of the S locus can be obtained by utilizing the assembly information of *Brassica oleracea* registered with the NCBI (https://www.ncbi.nlnmnih.gov/assembly/GCF_000695525.1/).

When polymorphism can be obtained in the case of using markers residing in the vicinity of the S locus such as those set forth in SEQ ID NO:10 to SEQ ID NO:15 between the lines to be mated, it is also possible to utilize these. By suppressing the linkage drag as far as possible to a small region by such a means, it is possible to impart a closely linked trait of the recurrent parent.

Therefore, according to a preferred embodiment of the present invention, the genotype is distinguished using a DNA marker located in a region in the extreme vicinity of the S locus (0 to 10 cM, and preferably 0 to 4 cM, from the S locus) including a gene associated with self-compatibility, and an individual having self-compatibility, in which the genomic region in the vicinity of the S locus has the genotype of the recurrent parent, that is, an individual in which the phenotype exhibits a plant shape that is extremely close to the recurrent parent, can be selected.

Regarding such a DNA marker, a DNA marker having any one or more of nucleotide sequences set forth in SEQ ID NO:10 to SEQ ID NO:15 may be mentioned as a preferred one.

Here, when it is said that a DNA marker "has" a nucleotide sequence, it is implied that the marker has that nucleotide sequence. According to the present invention, it is implied that a DNA marker may have any one or several (for example, 1, 2, or 3; preferably 1 or 2; and more preferably 1) of the bases in a corresponding nucleotide sequence substituted, deleted, added, or eliminated, or even a sequence including a corresponding nucleotide sequence as a portion and maintaining predetermined properties is also acceptable. In such a case, the term "have" may be replaced with the term "include". Furthermore, in a case in which substitution, deletion, addition, or elimination of one base is allowed, the term "have" may be replaced with the term "consist substantially of".

That is, such a DNA marker can be used in order to subject a region in the vicinity of the S locus of a *Brassica oleracea* plant to a genotype analysis.

Creation of a doubled haploid in anther culture and pollen culture can be carried out according to Palmer C et al., (1996) "In Vitro Haploid Production in Higher Plants", Vol. 3 (Kluwer Academic Publishers, editors: S Jain, S Sopory, and RVeilleux), pp. 143-172.

A novel self-compatible line developed as such can be utilized as a male parental line in the F1 seed production system. On the other hand, if self-propagated seeds obtained by self-pollination are produced in large quantities, the seeds cannot be used directly as a female parent. In order for the seeds to be used as a female parent, it is necessary to produce an A-line having CMS cytoplasm so that self seed is not produced.

In the case in which a CMS line of the recurrent parent is already in possession, when backcrossing is carried out two times at least using a newly produced self-compatible line as a B-line, it is possible to develop an A-line in which only the S locus and the region thereof have been substituted.

For conventional self-incompatible lines, it has been necessary to put in enormous efforts to propagate stock seeds. However, in the case of a parental line into which self-compatibility has been introduced, stock seed propagation of the parental line is easily accomplished using insect pollination. It is also possible to perform large-scale F1 seed production by using the A-line seeds of the parental line propagated as such.

Here, the A-line and the B-line are the cytoplasmic male sterile line and maintenance line, respectively, in a hybrid seed production system utilizing cytoplasmic male sterility. Since the nuclear genome configurations of the two lines are almost identical, the phenotypes of the plants are similar; however, the A-line does not produce pollen due to the influence of the cytoplasm. Stock seeds obtained by mating the A-line with the pollen of the B-line are used as the seed parent for F1 seed production.

The "parental line" according to the present invention refers to a line developed in order to produce seed of F1 varieties, and usually, an F1 variety is produced by using two parent lines having different agronomic traits as materials, and crossing these.

According to the present invention, "stock seed propagation" is propagation of parental line seeds needed to produce the seeds of an F1 variety.

Self-Compatible *Brassica oleracea* Plant

The self-compatible *Brassica oleracea* plant according to the present invention is a plant produced by the producing method of the present invention that will be described below and progenies thereof, as described above.

Furthermore, the self-compatible *Brassica oleracea* plant according to the present invention is a *Brassica oleracea* plant (excluding Chinese kale and cauliflower) having self-compatibility, the plant having a DNA of any one of the following (a) to (c) in the S locus, or a progeny thereof:

(a) a DNA including a nucleotide sequence set forth in SEQ ID NO:1 or SEQ ID NO:2, (b) a DNA including a nucleotide sequence having a sequence identity of 95% or higher with a nucleotide sequence set forth in SEQ ID NO:1 or SEQ ID NO:2, the DNA being involved in the expression of self-compatibility in a plant, or (c) a DNA including a nucleotide sequence obtained by deletion, substitution, insertion, and/or addition of one or a plurality of bases in a nucleotide sequence set forth in SEQ ID NO:1 or SEQ ID NO:2, the DNA being involved in the expression of self-compatibility in a plant.

According to a preferred embodiment of the present invention, the *Brassica oleracea* plant according to the present invention is a plant that has become self-compatible by introducing an S allele including the DNA of any one of the above-described items (a) to (c) into the self-incompatibility gene locus, or a progeny thereof.

Furthermore, the "progeny" of the self-compatible *Brassica oleracea* plant according to the present invention not only includes self progenies produced by self-fertilization, but also progenies originating from anther culture and pollen culture, and crossbreeds obtainable by mating the self-compatible *Brassica oleracea* plant according to the present invention with a *Brassica oleracea* plant that can be mated with the aforementioned plant. Therefore, the "progeny" also includes, for example, a plant obtainable by performing mating using the self-compatible *Brassica oleracea* plant according to the present invention as a pollen parent (male parent) and a *Brassica oleracea* plant that can be mated with the aforementioned plant as a seed parent (female parent). Furthermore, in a case in which a CMS line of the parental line for backcrossing already exists, when backcrossing is performed two times using a newly produced self-compatible line as B-line, it is possible to grow A-line in which only the S locus and the vicinity thereof have been substituted. A self-compatible *Brassica oleracea* plant having cytoplasmic male sterility obtainable as such can also be included in the progeny. Moreover, in the "progeny", for example, a plant obtained by cell fusion between the self-compatible *Brassica oleracea* plant according to the present invention and a plant that can be fused with the aforementioned *Brassica oleracea* plant, an intergeneric hybrid plant and an interspecific hybrid plant are also included.

According to another aspect of the present invention, the present invention also relates to a part of the plant body of the self-compatible *Brassica oleracea* plant according to the present invention or a progeny thereof, or seeds of the plant and the progeny.

Here, the "part of the plant body" includes organs such as flowers, leaves, stems, and roots, or portions or tissues thereof, or cells obtained from these organs or tissues, aggregates of the cells, and the like.

According to a preferred embodiment of the present invention, the self-compatible *Brassica oleracea* plant according to the present invention is typically a plant except for cauliflower and Chinese kale, and preferred examples include broccoli, cabbage, Brussels sprout, kohlrabi, ornamental cabbage, and kale, while more preferred examples include broccoli and cabbage.

According to a preferred embodiment of the present invention, the self-compatible *Brassica oleracea* plant according to the present invention or a progeny thereof can be any one of the following:

1) a *Brassica oleracea* plant excluding Chinese kale, wherein the plant has a self-compatibility gene locus "BoS-SC1" in the S locus, and the gene locus "BoS-SC1" is found in the Chinese kale variety identified by Accession No. FERM BP-22347, or a progeny thereof;

2) a *Brassica oleracea* plant excluding Chinese kale, wherein the plant has a self-compatibility gene locus "BoS-SC1" in the S locus, and the gene locus "BoS-SC1" is found in the broccoli variety identified by Accession No. FERM BP-22349, or a progeny thereof;

3) a *Brassica oleracea* plant excluding cauliflower and *Brassica oleracea* wild species, wherein the plant has a self-compatibility gene locus "BoS-SC2" in the S locus, and the gene locus "BoS-SC2" is found in the cauliflower variety identified by Accession No. FERM BP-22350, or a progeny thereof;

4) a *Brassica oleracea* plant excluding cauliflower and *Brassica oleracea* wild species, wherein the plant has a self-compatibility gene locus "BoS-SC2" in the S locus, and the gene locus BoS-SC2" is found in the broccoli variety identified by Accession No. FERM BP-22348, or a progeny thereof;

5) broccoli identified by Accession No. FERM BP-22349, or a progeny thereof; and 6) broccoli identified by Accession No. FERM BP-22348, or a progeny thereof.

Preferably, the above-mentioned gene locus "BoS-SC1" has a nucleotide sequence of the following (i) to (iii):

(i) a nucleotide sequence set forth in SEQ ID NO:1, (ii) a nucleotide sequence having a sequence identity of 95% or higher with a nucleotide sequence set forth in SEQ ID NO:1, and (iii) a nucleotide sequence obtained by deletion, substitution, insertion, and/or addition of one or a plurality of bases in a nucleotide sequence set forth in SEQ ID NO:1.

Furthermore, preferably, the above-mentioned gene locus "BoS-SC2" has a nucleotide sequence of the following (I) to (III):

(I) a nucleotide sequence set forth in SEQ ID NO:2, (II) a nucleotide sequence having a sequence identity of 95% or higher with a nucleotide sequence set forth in SEQ ID NO:2, or (III) a nucleotide sequence obtained by deletion, substitution, insertion, and/or addition of one or a plurality of bases in a nucleotide sequence set forth in SEQ ID NO:2.

With regard to the phrases "having a sequence identity of 95% or higher with a nucleotide sequence set forth in SEQ ID NO:1" of the above item (ii) and "having a sequence identity of 95% or higher with a nucleotide sequence set forth in SEQ ID NO:2" of the above item (II), similarly to the case of the above-described item (b), when the sequence identity is calculated using a nucleotide sequence set forth in SEQ ID NO:1 or SEQ ID NO:2 and a known algorithm for homology search (for example, default parameters, that is, parameters of initial settings, are used), such as BLAST or FASTA, a DNA having a sequence identity of at least 95%, preferably at least 96%, more preferably at least 97%, even more preferably at least 98%, and particularly preferably at least 99%, is included.

Furthermore, the term "a plurality" as used in the phrases "a nucleotide sequence obtained by deletion, substitution, insertion, and/or addition of one or a plurality of bases in a nucleotide sequence set forth in SEQ ID NO:1" of the above item (iii) and "a nucleotide sequence obtained by deletion, substitution, insertion, and/or addition of one or a plurality of bases in a nucleotide sequence set forth in SEQ ID NO:2" of the above item (III) means, similarly to the case of the above-described item (c), for example, about 10 bases, preferably 7 bases, preferably 5 bases, and more preferably 3 bases.

According to another embodiment of the present invention, there is also provided a marker for detecting self-compatibility in a *Brassica oleracea* plant, the marker having a nucleotide sequence of any one of the following (A) to (C):

(A) a nucleotide sequence set forth in SEQ ID NO:1 or SEQ ID NO:2, (B) a nucleotide sequence having a sequence identity of 95% or higher with a nucleotide sequence set forth in SEQ ID NO:1 or SEQ ID NO:2, or (C) a nucleotide sequence obtained by deletion, substitution, insertion, and/or addition of one or a plurality of bases in a nucleotide sequence set forth in SEQ ID NO:1 or SEQ ID NO:2.

Furthermore, the items (B) and (C) as mentioned herein are defined to have the same meanings as the nucleotide sequences in the above-described items (b) and (c).

According to still another aspect of the present invention, there is provided a method for producing seeds of a *Brassica oleracea* plant, the method including self-propagating a self-compatible *Brassica oleracea* plant obtained by the producing method of the present invention, or a progeny thereof, and thereby producing seeds thereof.

Here, in a case in which a self-compatible line produced by the present invention is self-propagated, the pollen of the plant itself or the same line may be mated to the stigma. As a specific method, an anther of an open flower are plucked with tweezers, and pollens are pollinated by bringing that anther into contact with the stigma. In addition to that, when a paper bag for mating is put on the inflorescence where flowers have bloomed, and physical impacts such as tapping the bag with a hand are applied, the pollen of the plant itself adheres to the stigma, and thus fertilization can be induced.

Furthermore, in the case of performing seed production in a large scale, self-fertilized seeds can be obtained efficiently in large quantities, by planting a large number of plants of the same line in an isolation chamber in which intrusion of insects from the external world is blocked, and performing insect pollination utilizing honeybees and the like.

In a case in which large-scale seed production is further carried out, self-fertilized seeds can be obtained efficiently in large quantities, by planting a large number of plants of the same line outdoors in a farm field where satisfactory isolation management has been achieved so that unexpected crossing does not occur, and performing insect pollination utilizing honeybees and the like.

According to still another aspect of the present invention, there is provided a method of maintaining or propagating a parental line of a useful first filial generation variety by using the producing method of the present invention.

Furthermore, according to still another aspect of the present invention, there is also provided a method for producing first filial generation seeds of *Brassica oleracea* that utilizes cytoplasmic male sterility (CMS), wherein a parental line of the first filial generation line is propagated by utilizing a *Brassica oleracea* plant having self-compatibility.

Through such methods of the present invention, it is possible to omit (1) steps required to break down SI (bud pollination, $CO_2$ treatment, NaCl treatment, and the like); and (2) steps of considering the strategy for propagation (plans for seed production scale and the like) in consideration of the degree of strength of SI, which have been conventionally necessary.

Furthermore, according to the present invention, a breeding method of conceiving the combination of parents for producing F1 without having to consider the S haplotypes between elite lines, can be provided.

EXAMPLES

The present invention will be specifically described by the following Examples; however, the present invention is not intended to be limited by these Examples.

Example 1: Search for Self-Compatibility Factor

In order to search for a self-compatibility factor, broccoli, cabbage, cauliflower, Chinese kale, ornamental cabbage, and other *Brassica oleracea* wild species were used as materials, and a mating test and an analysis of the S locus by means of an S haplotype-distinguishing marker were carried out.

From the results of a mating test by self-pollination, a self-compatible line with extremely weak SI or a perfectly self-compatible line was selected.

As an S haplotype-distinguishing marker, an S haplotype analysis of various lines was carried out using known primers set forth in SEQ ID NO:3 to SEQ ID NO:9.

As a result, even for lines having the same S haplotype, the factors other than S-locus seemed to affect the character of SI or SC in most cases, according to the conventional knowledge, (Horisaki et al., 2004 (Non Patent Document 5)).

On the other hand, with regard to "K-3" line of Chinese kale, "T-16" line of a *Brassica oleracea* wild species, and "CF-33" line of cauliflower, the segregating progenies of populations obtained by mating those lines were investigated, and as a result, any individual having the same S haplotype as these materials stably exhibited the phenotype of SC.

From this, it was speculated that self-compatibility of these materials is caused by loss of the function of a gene residing at the S locus.

As primers for amplifying SLG (S-locus glycoprotein), which is one of the genes residing at the S locus, PS5 (SEQ ID NO:3) and PS15 (SEQ ID NO:4) were used to analyze the nucleotide sequences of amplified DNA fragments.

As a result, K-3 had the nucleotide sequence of SEQ ID NO:1 (this genotype is referred to as "BoS-SC1"), and T-16 and CF-33 had the nucleotide sequence of SEQ ID NO:2 (this genotype is referred to as "BoS-SC2").

As a result of BLAST search using NCBI, the nucleotide sequence of SEQ ID NO:1 was registered as XM_013734339 (SLG of BoS-13 like), and the nucleotide sequence of SEQ ID NO:2 was registered as D85202 (SLG of BoS-16).

With regard to the nucleotide sequence of SEQ ID NO:2, in the document by Kusaba et al., (1997) (Non Patent Document 6), this nucleotide sequence was dealt with as one of multiple alleles of a plurality of self-incompatibility genes existing in the *Brassica oleracea* species; however, it is not stated therein that this-allele has self-compatibility.

With regard to the nucleotide sequence of SEQ ID NO:1, in the same document, this nucleotide sequence is considered to be related to a gene that is presumed to be SLG by genome assembling of line name: TO1000, and it is described that the TO1000 line is self-compatible; however, it is not stated therein that the line has self-compatibility caused by the S locus. In fact, a case in which even though the line seems to have self-compatibility as described above, the line is very weakly self-incompatible, and a case in which the line acquires self-compatibility by deletion of a signal transduction factor other than the S locus, have been reported many times (M. Kitaura et al., 2007 (Non Patent Document 7) and E. Indriolo, 2012 (Non Patent Document 8)).

Therefore, in the document by Kusaba et al. described above and the like, it was difficult to determine whether a gene locus including SEQ ID NO:1 is involved in self-compatibility.

Under such circumstances, the inventors of the present invention identified for the first time, as described in the following Examples 2 to 6, that gene loci including SEQ ID NO:1 and SEQ ID NO:2 are per se gene loci exhibiting self-compatibility, by performing experiments of going through a large-scale population for backcrossing and many generations.

Example 2: Introduction of SC into Broccoli "BR-9" Breeding Line

A mating test was carried out using "K-3" (S haplotype was BoS-SC1, Accession No. FERM BP-22347), which is a line of Chinese kale, as a material of an SI function-deleted line, and using "BR-9" (S haplotype was BoS-18), which is a parental line of broccoli owned by SAKATA SEED CORPORATION, as a parental line for backcrossing.

On the occasion of efficiently proceeding with backcrossing, a DNA assay was carried out basically using an S haplotype marker, individuals in which the S locus was heterozygous of BoS-SC1/BoS-18 were selected, and "BR-9" was subjected to repeated backcrossing while the phenotype was checked.

The seeds of the above-described line of Chinese kale "K-3" was internationally deposited (original deposition) as of Sep. 29, 2017, with Accession No. FERM BP-22347 obtainable from the National Institute of Technology and Evaluation, International Patent Organisms Depositary (#120, 2-5-8, Kazusakamatari, Kisarazu-shi, Chiba Prefecture. Japan) (indication for identification assigned by depositor: K-3, Accession No.: FERM BP-22347).

First, Chinese kale "K-3" having BoS-SC1 and broccoli "BR-9" were mated, thereby F1 seeds were produced, and then backcrossing of "BR-9" was carried out over several years. In order to efficiently proceed with backcrossing, selection by means of twenty kinds of RAPD primers was carried out, and individuals exhibiting a genotype close to "BR-9", which was the recurrent parent, were selected.

As a result, individuals in which these RAPD markers exactly matched with those of "BR-9" in the BC2F1 generation, were selected.

Seeds of the BC3F1 generation were sown, DNA selection of the S locus was performed using seedlings, the seedlings were planted in the farm field, and a phenotype survey was carried out. A significant number of these selected individuals matured earlier than "BR-9", the compactness of their heads was loose, and the commodity value as broccoli was low (FIG. 1B).

From these results, the possibility was suggested that factors involved in the early ripening properties and the compactness of heads may exist in the extreme vicinity of BoS-SC1 gene residing on chromosome 6.

The next year, seeds of BC4F1 were sown, a DNA assay based on an S haplotype marker was performed for 1581 individuals that had germinated, and after selection, the seedlings were planted in a farm field.

At the timing of heads appearing, phenotypes such as the ripening time, compactness of heads, and smoothness were checked, and thirty individuals having plant shapes relatively close to "BR-9" were selected.

At the same time, a genotyping analysis was carried out using DNA markers located on both sides of the region of the S locus, BoC6MK1 (PCR based on SEQ ID NO:10 and SEQ ID NO:11 was performed. Residing at a distance of 1.1 cM from the S locus) and BoC6MK2 (PCR based on SEQ ID NO:12 and SEQ ID NO:13 was performed. Residing at a distance of 0.3 cM from the S locus), and four individuals having the markers on both sides substituted with "BR-9" type could be selected from the thirty individuals for which phenotype selection was carried out. Next, from these individuals, self-propagated seeds and anther cultured or pollen cultured progenies were obtained.

Seeds of the progeny of the selected strain were sown, individuals in which the S locus had become BoS-SC1 homozygous were selected, and then self-compatible "SC-BR-9" line thus obtained was cultivated in a farm field. As described above, a phenotype survey was conducted in January, when flower buds came out, and in these individuals, the plant shape and the ripening time were so similar to those of the BC parent "BR-9" that the lines were indistinguishable (FIG. 1C and FIGS. 2A-C).

Figure 2B:
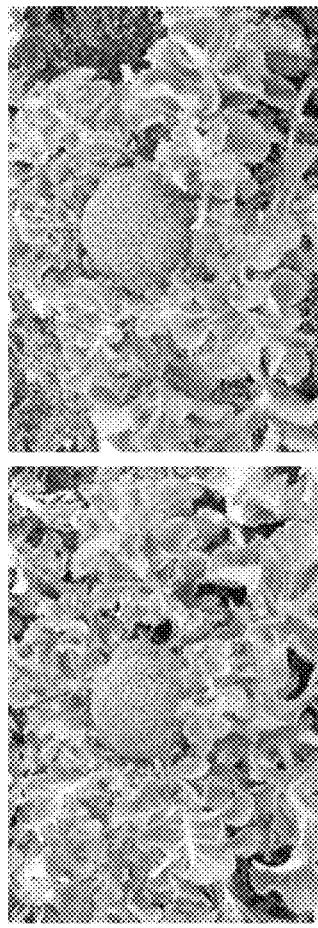
Figure 2C:
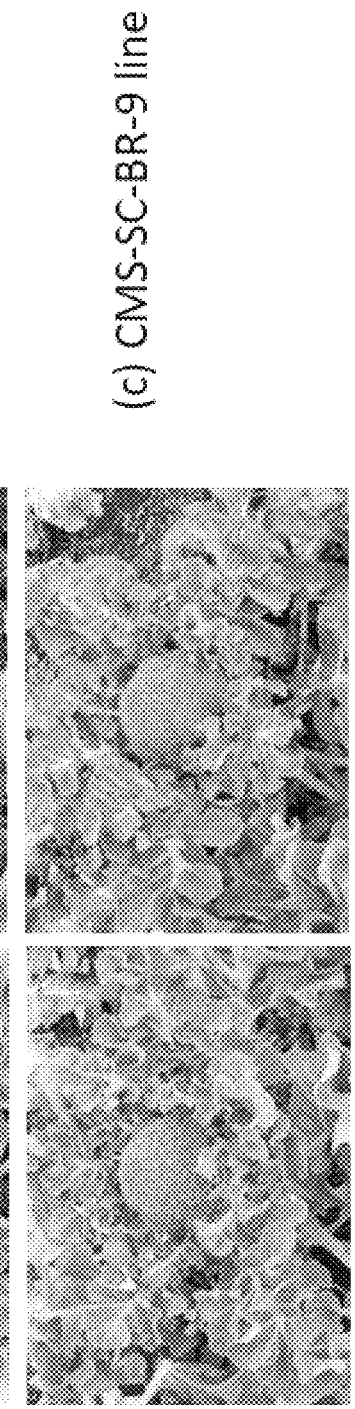

Using this line, backcrossing into the CMS A-line of "BR-9" was carried out, and "CMS-SC-BR-9" (Accession No. FERM BP-22349), which is a self-compatible cytoplasmic male sterility line of "SC-BR-9", was also completed (FIGS. 2A-C).

The seeds of the above-described line of broccoli "CMS-SC-BR-9" have been internationally deposited (original deposition) as of Sep. 29, 2017, with Accession No. FERM BP-22349 obtainable from the National Institute of Technology and Evaluation, International Patent Organisms Depositary (#120, 2-5-8, Kazusakamatari, Kisarazu-shi, Chiba Prefecture. Japan) (indication for identification assigned by depositor: CMS-SC-BR-9, Accession No.: FERM BP-22349).

From the above results, even if the S locus was Chinese kale-derived BoS-SC1 homozygous, development of a self-compatible line having high commodity value as broccoli was succeedful for the first time, by selecting an individual in which the genomic region in the extreme vicinity was recombined into the genotype of "BR-9", which was the recurrent parent.

Example 3: Seed Production Test by Entomophily of Self-Compatible Line

Figure 3:
FIG. 3 shows the results of an isolation chamber seed production test of Example 3 ("SC-BR-9" and "CMS-SC-BR-9").

A seed production test in an isolation chamber was carried out by insect pollination using "SC-BR-9" (B-line), which is a normal cytoplasm line in which an S gene (BoS-18) inherently possessed by "BR-9" has been substituted with BoS-SC1, and "CMS-SC-BR-9" (A-line), which is a CMS line of the aforementioned line (FIG. 3).

Two isolation chambers were used for the purpose of performing repeated tests, 24 plants each of A-line and B-line were cultivated, entomophilic mating by honeybees was carried out, and the weights of the seeds thus obtained were examined.

The average yields in the first section were 30.4 g/plant for A-line and 36.2 g/plant for B-line, and the average yields in the second section were 35.8 g/plant for A-line and 29.7 g/plant for B-line. Thus, very high yields were obtained (Table 1).

When these results are compared with the results of a seed production test for "CMS-BR-9", which is an original CMS SI line, and "BR-9" (BoS-18 homozygous), in which the seed production yields were only 0.02 g/plant for A-line and 0.61 g/plant for B-line for the average of seven plants, the difference is clear.

From this example it was verified that the lines produced according to the present invention were lines having excellent seed production properties.

TABLE 1

| Isolation chamber | Line | Number of plants | Total yield (g) | g/Strain | Remarks |
| --- | --- | --- | --- | --- | --- |
| Cage-1 | CMS-SC-BR-9 | 24 | 729.67 | 30.4 | SC Line (A line) |
| Cage-1 | SC-BR-9 | 22 | 795.68 | 36.17 | SC Line (B line) |
| Cage-2 | CMS-SC-BR-9 | 21 | 752.72 | 35.84 | SC Line (A line) |
| Cage-2 | SC-BR-9 | 24 | 713.26 | 29.72 | SC Line (B line) |
| Cage-3 | CMS-BR-9 | 7 | 0.17 | 0.02 | SI Line (A line) |
| Cage-3 | BR-9 | 7 | 4.29 | 0.61 | SI Line (B line) |

Example 4: Introduction of SC into Broccoli "BR-6" Breeding Line and Growing of CMS Line Thereof For another broccoli parental line, "BR-6", introduction of self-compatibility was attempted by using "T-16" of the *Brassica oleracea* wild species as a donor for the self-compatibility factor.

Similarly to Example 2, backcrossing of "BR-6" was carried out while using an S haplotype distinguishing marker, the phenotype was selected, a selection based on a genotyping analysis using markers in the region of the S locus, BoC6MK1 (PCR based on SEQ ID NO:10 and SEQ ID NO:11 was performed. Residing at a distance of 1.1 cM from the S locus) and BoC6MK3 (PCR based on SEQ ID NO:14 and SEQ ID NO:15 was performed. Residing at a distance of 2.2 cM from the S locus) was carried out, and thus the phenotype of BC4F1S1 generation thus obtained was investigated.

As a result, it became clear that if the S locus was BoS-SC2 homozygous derived from "T-16", when an individual in which the genomic region in the extreme vicinity has been recombined into the genotype of the parental line for backcrossing "BR-6" is selected, the individual exhibits a maturity and plant shape that are extremely close to those of "BR-6", the recurrent parent, in the external appearance.

Figure 4:
FIG. 4 shows the results of an isolation chamber seed production test of Example 4 ("SC-BR-6" and "CMS-SC-BR-6").

A seed production test in an isolation chamber was carried out (FIG. 4) in the same manner as in Example 3, using "SC-BR-6" (normal cytoplasm, B-line) produced as such and a CMS A-line thereof, "CMS-SC-BR-6" (male sterile cytoplasm, A-line) (Accession No. FERM BP-22348).

The seeds of the above-described broccoli line "CMS-SC-BR-6" have been internationally deposited (original deposition) as of Sep. 29, 2017, with Accession No. FERM BP-22348 obtainable from the National Institute of Technology and Evaluation, International Patent Organisms Depositary (#120, 2-5-8, Kazusakamatari, Kisarazu-shi, Chiba Prefecture. Japan) (indication for identification assigned by depositor: CMS-SC-BR-6, Accession No.: FERM BP-22348). Similarly, the seeds of a line for which the indication for identification assigned by the depositor is Milkyway have been internationally deposited (original deposition) as of Sep. 29, 2017, with Accession No. FERM BP-22350 obtainable from the National Institute of Technology and Evaluation, International Patent Organisms Depositary (#120, 2-5-8, Kazusakamatari, Kisarazu-shi, Chiba Prefecture. Japan) (Accession No.: FERM BP-22350).

Fourteen plants each of the A-line and the B-line were cultivated, insect pollination was carried out, and the average seed yields of the respective lines were 39.5 g/plant for the A-line and 39.8 g/plant for the B-line. Thus, the lines were found to have high seed production properties (Table 2).

From the above results, it became clear that even if the S locus is BoS-SC2 homozygous, a self-compatible line of a broccoli with high commodity value is produced.

TABLE 2

| Isolation chamber | Line | Number of plants | Total yield (g) | g/Strain | Remarks |
|---|---|---|---|---|---|
| Cage-4 | CMS-SC-BR-6 | 14 | 553.68 | 39.55 | SC Line (A line) |
| Cage-4 | SC-BR-6 | 14 | 557.58 | 39.83 | SC Line (B line) |
| Cage-5 | CMS-BR-6 | 186 | 104 | 0.56 | SI Line (A line) |
| Cage-5 | BR-6 | 190 | No data | No data | SI Line (B line) |

Example 5: Development of Self-Compatible SC Cabbage (4 Lines)

"K-3" (S haplotype was BoS-SC1, Accession No. FERM BP-22347), which is a line of Chinese kale, was used as an SI function-deleted line, and a mating test was carried out using each of "CB-20" (Yoshin cabbage, S haplotype is BoS-5), "CB-35" (Kangyoku cabbage, S haplotype is BoS-51), "CB-23" (spring cabbage, S haplotype is BoS-8), and "CB-97" (ball cabbage, S haplotype is BoS-15), which are parental lines of cabbage possessed by SAKATA SEED CORPORATION, as the recurrent parent.

To proceed efficiently with backcrossing, a DNA assay was carried out using an S haplotype marker, individuals in which the S locus was heterozygous of BoS-SC1/BoS-5, BoS-SC1/BoS-51, BoS-SC1/BoS-8, and BoS-SC1/BoS-15, respectively, were selected, and while the phenotype was checked, "CB-20", "CB-35", "CB-23", and "CB-97" were subjected to repeated backcrossing.

First, Chinese kale "K-3" having BoS-SC1, and each of cabbages "CB-20", "CB-35", "CB-23", and "CB-97" were mated to produce F1 seeds, and thereafter, backcrossing of "CB-20", "CB-35", "CB-23", and "CB-97" was carried out with each of the lines over several years.

In order to efficiently proceed with backcrossing, selection using twenty kinds of RAPD primers was carried out, and for each of the backcrossing lines, individuals exhibiting genotypes close to "CB-20", "CB-35", "CB-23", and "CB-97", which were the parental lines for backcrossing, respectively, were selected.

As a result, regarding "CB-20", "CB-35", and "CB-23", individuals in BC4F1 generation, in which these RAPD markers exactly matched those of the respective parental lines for backcrossing, were selected.

Furthermore, regarding "CB-97", individuals in BC4F1 generation, in which these RAPD markers almost matched those of the recurrent parent, were selected.

The generations were further passed on, trial production was carried out in farm fields, and it was verified that the phenotypes were equal to those of the original recurrent parent.

For each of the lines, a homozygote of BoS-SC1 was obtained from self-propagation or from anther culture and pollen culture, and thus development of a self-compatible line of cabbage was successful for the first time.

Furthermore, backcrossing into the respective A-lines (cytoplasmic male sterile) of "CB-20", "CB-35", "CB-23", and "CB-97" was carried out, and lines of self-compatible "SC-CB-20", "SC-CB-35", "SC-CB-23", and "SC-CB-97" and lines of cytoplasmic male sterile lines "CMS-SC-CB-20", "CMS-SC-CB-35", "CMS-SC-CB-23", and "CMS-SC-CB-97" were also developed.

Example 6: Introduction of Separate Lines of SC Cabbages and Hand Mating Test

Other cabbage breeding lines were further mated by using the self-compatible cabbage lines produced in Example 5 as SC donors, and thereby, cabbages possessing self-compatibility were developed.

As an example, mating was achieved using "CB-3" (ball cabbage, S haplotype is BoS-2b) as the seed parent, and using BC5F1 generation of "CB-97" (ball cabbage, S haplotype is BoS-SC1/BoS-15) having self-compatibility in the middle of growing in Example 5 as the pollen parent, and F1 seed was created.

To proceed efficiently with backcrossing, a DNA assay was carried out using an S haplotype marker, individuals in which the S locus was heterozygous of BoS-SC1/BoS-2b were selected, and "CB-3" was subjected to repeated backcrossing while the phenotype was checked.

"CB-3" was further subjected to backcrossing with BC4F1 generation of the "CB-3" line having an allele for self-compatibility, and thereby a cabbage "SC-CB-3" line having self-compatibility was produced.

Together with "CB-3", which was the recurrent parent from the SI system, newly produced self-compatible "SC-CB-3" was used as a material, and a mating test using hand mating was carried out.

The results were as follows.

Figure 5A:
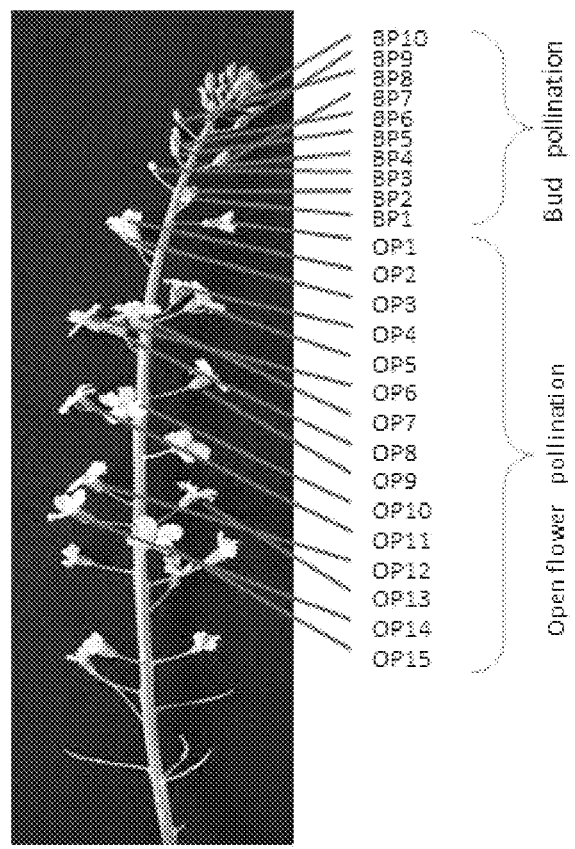
FIG. 5A shows the state of seed setting of "CB-3", which is an elite line of the SI system of cabbage in Example 6, and "SC-CB-3" into which an SC factor has been introduced. The diagram shows the form of inflorescence, and that flower opening proceeded sequentially from the buds at lower positions.

The inflorescence of plants of the family Brassicaceae has a form as shown in FIG. 5A, and flower opening proceeded in order from the buds at the lower positions.

With regard to such inflorescence, open flower pollination (OFP) and bud pollination (BP) were carried out on the same day, and thereby an assay of self-incompatibility and self-compatibility was carried out. At the time of performing bud pollination, the calyxes and the petals were cut off with tweezers, the pistil was exposed, and thereby pollination was performed. The mated buds and flowers were assigned with numbers according to the rules such as shown in FIG. 5A, and at the time point where one month or longer had elapsed after mating and the seeds ripened, the numbers of developed seeds at various positions were counted.

Figure 5B:
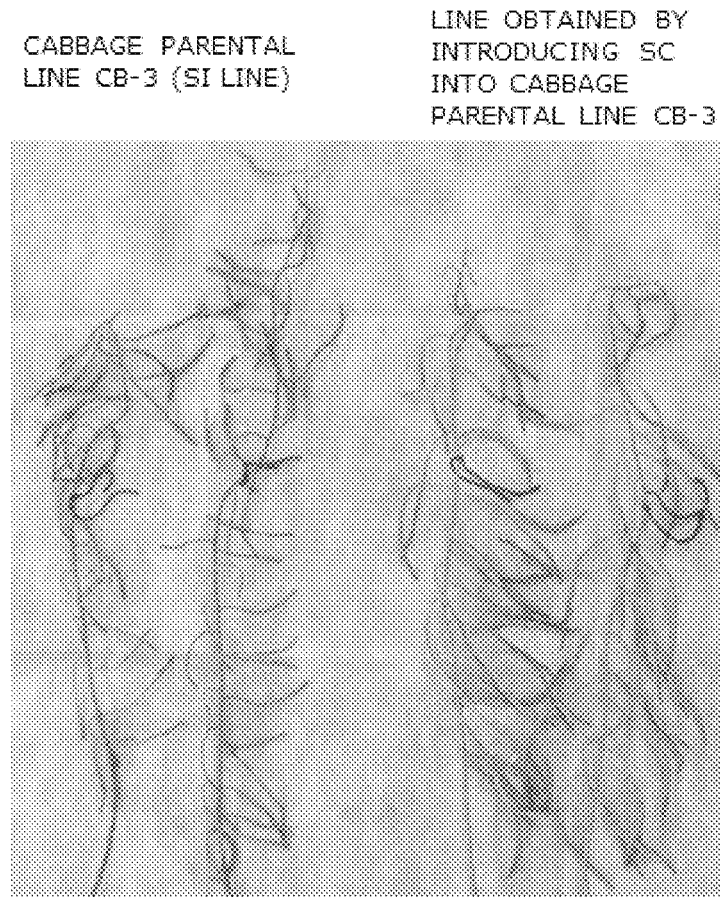
FIG. 5B shows the state of pods at a time point at which one month or more has elapsed after mating in Example 6.

FIG. 5B is the state of seed pods at the time point where one month or longer had elapsed after mating.

In the recurrent parent from the SI system, at the positions lower than the yarn that indicated the boundary of OFP/BP at the time of mating, seeds were almost not formed. On the other hand, in the BP zone, since the SI gene was not expressed in the stigma at the time point of performing mating, it could be confirmed that seeds were formed. In contrast, in the line into which SC had been introduced, it was found that large amounts of seeds were formed in the BP zone as well as in the OFP zone.

FIG. 5C shows the results of counting the number of seeds formed in each of these pods.

As shown in the results, in "CB-3" which is the recurrent parent from the SI system, seeds were hardly formed in the pods in the OFP zone, whereas in the BP zone, seeds were formed at a rate of more or less 10 seeds per pod. On the other hand, in the line into which the SC trait had been introduced, about 10 to 20 seeds were formed in the OFP zone, and it was verified that the self-compatibility trait was imparted.

From the results described above, it was found that for broccoli and cabbage, for which the existence of self-compatible lines have not been hitherto known, self-compatibility can be introduced by following the present invention, and lines having both self-compatibility and the product quality of commercial crops can be produced.

The invention claimed is:

1. A *Brassica oleracea* plant having self-compatibility, the *Brassica oleracea* plant comprising:
   in a self-incompatibility gene locus (S locus) of the *Brassica oleracea* plant:
   (a) DNA comprising a nucleotide sequence set forth in SEQ ID NO:1 or SEQ ID NO:2; or
   (b) DNA comprising a nucleotide sequence having a sequence identity of 95% or higher with the nucleotide sequence set forth in SEQ ID NO:1 or SEQ ID NO:2, the DNA being involved in expression of self-compatibility in a plant, and
   wherein the *Brassica oleracea* plant is broccoli or cabbage.

2. The *Brassica oleracea* plant according to claim 1, wherein the *Brassica oleracea* plant is obtainable by mating a self-compatible *Brassica oleracea* plant with a self-incompatible *Brassica oleracea* plant and selecting an individual having self-compatibility from a cross-progeny.

3. The *Brassica oleracea* plant according to claim 1, wherein the *Brassica oleracea* plant is self-compatible with an S-allele including the DNA of (a) or (b) introduced into the S locus of the *Brassica oleracea* plant.

4. A part of a plant body of the *Brassica oleracea* plant according to claim 1, wherein the part of the plant body comprises in the S locus:
   (a) the DNA comprising the nucleotide sequence set for th in SEQ ID NO: 1 or SEQ ID NO: 2; or
   (b) the DNA comprising the nucleotide sequence having a sequence identity of 95% or higher with the nucleotide sequence set forth in SEQ ID NO:1 or SEQ ID NO:2.

5. A seed of the *Brassica oleracea* plant according to claim 1, wherein the part of the plant body comprises in the S locus:
   (a) the DNA comprising the nucleotide sequence set for th in SEQ ID NO: 1 or SEQ ID NO: 2; or
   (b) the DNA comprising the nucleotide sequence having a sequence identity of 95% or higher with the nucleotide sequence set forth in SEQ ID NO:1 or SEQ ID NO:2.

* * * * *